United States Patent [19]

Dague

[11] Patent Number: 5,185,079
[45] Date of Patent: Feb. 9, 1993

[54] ANAEROBIC SEQUENCING BATCH REACTOR

[75] Inventor: Richard R. Dague, Ames, Iowa

[73] Assignee: Iowa State University Research Foundation, Inc., Ames, Iowa

[21] Appl. No.: 701,045

[22] Filed: May 16, 1991

[51] Int. Cl.$^5$ .............................................. C02F 3/28
[52] U.S. Cl. .................................... 210/603; 210/610; 210/613
[58] Field of Search ............... 210/603, 605, 610–613, 210/621, 630

[56] References Cited

U.S. PATENT DOCUMENTS

| | | | |
|---|---|---|---|
| 3,819,331 | 6/1974 | Weber | 23/284 |
| 3,973,043 | 8/1976 | Lynn | 426/55 |
| 4,022,665 | 5/1977 | Ghosh et al. | 195/27 |
| 4,024,060 | 5/1977 | Hughes | 210/197 |
| 4,096,215 | 6/1978 | Albrecht | 261/121 R |
| 4,274,838 | 6/1981 | Dale et al. | 210/612 |
| 4,316,961 | 2/1982 | Klass et al. | 210/603 |
| 4,334,997 | 6/1982 | Peterson | 210/603 |
| 4,491,522 | 1/1985 | Ishida et al. | 210/603 |
| 4,798,801 | 1/1989 | Hitzman | 435/313 |
| 4,917,805 | 4/1990 | Reid | 210/605 |
| 4,927,530 | 5/1990 | Ueda | 210/149 |
| 4,948,510 | 8/1990 | Todd et al. | 210/605 |
| 5,013,441 | 5/1991 | Goronszy | 210/605 |
| 5,076,927 | 12/1991 | Hunter | 210/603 |
| 5,110,459 | 5/1992 | Baxter | 210/605 |

*Primary Examiner*—Thomas Wyse
*Attorney, Agent, or Firm*—Henderson & Sturm

[57] ABSTRACT

An anaerobic sequence batch process carried out in a single vessel. The biological reactions occur under anaerobic conditions and the vessel is operated on a fill-and-draw basis in a sequential manner. When waste is entering the reactor, the vessel is mixed by biogas or liquid recirculation. Waste feeding continues until the reactor is filled to its predetermined full liquid level. The anaerobic reaction proceeds with intermittent or continuous mixing. Mixing is then discontinued, allowing the biomass to settle under quiescent conditions resulting in the formation of a low suspended solids supernatant. After sufficient time in the settling cycle, supernatant is withdrawn from the reactor lowering the reactor contents to the predetermined lower liquid level. Gas or liquid recirculation mixing is then begun again along with waste feeding. Excess biomass is wasted from the reactor on a periodic basis. The capacity of the reactor depends on the number of feeding-clarification-wasting cycles that can be achieved in a day.

18 Claims, 1 Drawing Sheet

ANAEROBIC SEQUENCING BATCH REACTOR

BACKGROUND ART

The first application of anaerobic biological processes to the treatment of organic wastes was the septic tank, invented in 1895. A variety of applications of the anaerobic concept have evolved over the past nearly 100 years. Early applications, beginning in 1918, were to the treatment of sludges from domestic sewage. Much later, beginning in the 1950's, a process that was variously called "anaerobic contact" and "anaerobic activated sludge" was applied to livestock slaughtering wastewaters. This process made use of a separate solids separation or clarifier unit. Still later, beginning in the 1970's, anaerobic treatment applications included various attached growth (upflow, downflow, and expanded bed) treatment approaches.

The anaerobic contact process developed in the 1950's makes use of a reactor tank in which contact between the anaerobic microorganisms and the wastewater occurs. The wastewater then flows through a vacuum degasifier to remove dissolved gases to enhance solids settling and then on to a separate solids searation unit in which biomass solids settle to the bottom for recycling to the contact tank. In these systems, multiple vessels are required resulting in high capital investment and inefficiencies due to the need to transfer the materials to a separate vessel for individual process steps.

Those concerned with these and other problems recognize the need for an improved anaerobic sequencing batch process.

DISCLOSURE OF THE INVENTION

The present invention provides an anaerobic sequence batch process carried out in a single vessel. The biological reactions occur under anaerobic conditions and the vessel is operated on a fill-and-draw basis in a sequential manner. When waste is entering the reactor, the vessel is mixed by biogas or liquid recirculation. Waste feeding continues until the reactor is filled to its predetermined full liquid level. The anaerobic reaction proceeds with intermittent or continuous mixing. Mixing is then discontinued, allowing the biomass to settle under quiescent conditions resulting in the formation of a low suspended solids supernatant. After sufficient time in the settling cycle, supernatant is withdrawn from the reactor lowering the reactor contents to the predetermined lower liquid level. Gas or liquid recirculation mixing is then begun again along with waste feeding. Excess biomass is wasted from the reactor on a periodic basis. The capacity of the reactor depends on the number of feeding-clarification-wasting cycles that can be achieved in a day.

The anaerobic sequencing batch reactor is applicable for the conversion of a wide variety of organic wastewaters to methane and carbon dioxide (biogas) through the actions of a mixed consortium of anaerobic microorganisms, primarily hydrolytic, acetogenic, and methanogenic bacteria that thrive in the complete absence of inorganic oxygen. Primary applications are to the conversion to biogas of wastewaters from biotechnology, grain and other food processing industries, and to livestock wastes.

Typical applications are treatment of wastewaters from grain processing plants, food processing plants (milk, eggs, etc.), livestock slaughtering plants, confined livestock feeding operations, and pharmaceutical and other biotechnology industries.

The unique features of the process are primarily the use of internal solids separation that enables efficient separation of biomass solids from the liquid while avoiding degasification (to remove $CO_2$ and $CH_4$) that is common in processes using external clarifiers. This feature, coupled with the unique sequencing approach provides a new process that is capable of high rates of waste processing and conversion to methane and carbon dioxide, a valuable fuel gas.

An object of the present invention is the provision of an improved anaerobic sequence batch process.

Another object is to provide an anaerobic process that is carried out in a single vessel.

A further object of the invention is the provision of an anaerobic process that does not require synthetic media for the attachment of biological growth.

Still another object is to provide an anaerobic process that requires a low capital equipment investment and results in efficient operation.

A still further object of the present invention is the provision of an anaerobic process wherein settling takes place in the reaction vessel giving a low solids supernatant which can be discharged without significant loss of biological mass.

These and other attributes of the invention will become more clear upon a thorough study of the following description of the best mode for carrying out the invention, particularly when reviewed in conjunction with the drawings and examples.

BEST MODE FOR CARRYING OUT THE INVENTION

Figure 1:
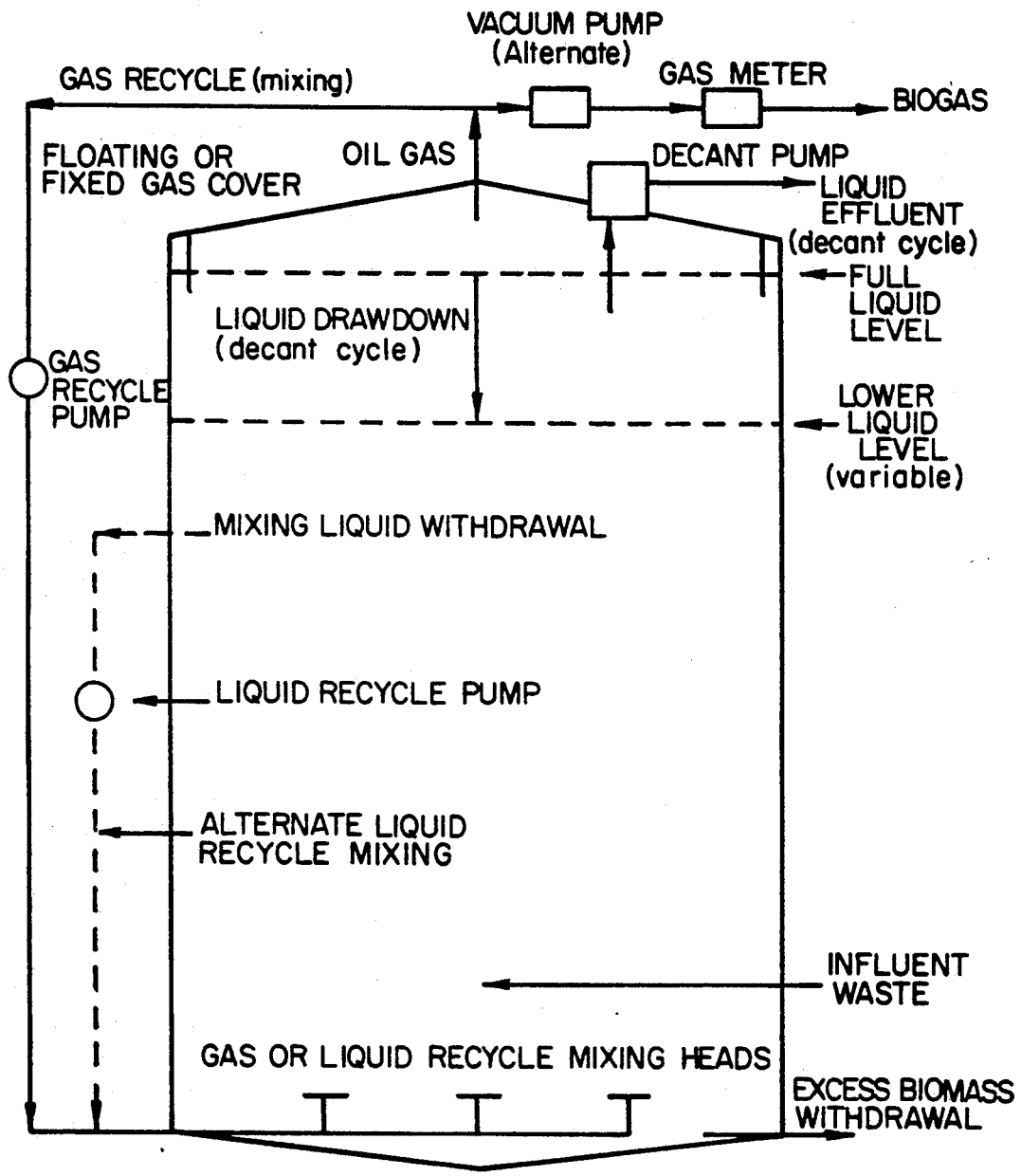
FIG. 1 is a schematic drawing illustrating the anaerobic sequencing batch reactor used to practice the process of the present invention.

The following examples are illustrative of the best mode for carrying out the invention. They are obviously not to be construed as limitative of the invention since various other embodiments can readily be evolved in view of the teachings provided herein.

The anaerobic sequencing batch reactor (ASBR) schematically illustrated in FIG. 1 has been demonstrated at laboratory scale through applications to several actual waste materials and a synthetic waste. The two actual wastes are a by-product from a manufacturing plant and a swine manure from the swine nutrition research facility. The synthetic waste was made from a non-fat dry milk. These three sources cover a wide range of waste characteristics.

EXAMPLE 1

The fundamental studies on the ASBR have made use of a non-fat dry milk (NFDM) substrate in order to carefully control the loading and operational conditions. The NFDM substrate is highly soluble, i.e., low in suspended solids.

A series of experimental runs were conducted using two laboratory-scale ASBRs. the reactors are made of plexiglass and are 36" in height and have a 5.5" inside diameter. The effective liquid volume of the reactors is 13.0 liters.

The NFDM is mixed with tap water to provide a specific organic strength based on chemical oxygen demand (COD). In addition to the NFDM substrate, the reactor feed also consists of sodium bicarbonate for pH buffering and a mineral solution which includes salts of iron, zinc, nickel, cobalt and manganese. In these studies, the organic strength (COD) of the feed was varied from 500 mg/L to 1,500 mg/L. COD loadings on the reactors have been varied form a low of 0.5 g COD/L/day to 1.5 g COD/L/day. The nomical hydraulic retention time (HRT) maintained in the reactors has been one day. Operating conditions are shown in Table 1. Results are shown in Table 2.

TABLE 1

Operating Conditions for the ASBR Studies

| Parameter | Organic Loading, g COD/L of Reactor/day | | | |
|---|---|---|---|---|
| | 1.5 | 1.5 | 1.0 | 0.5 |
| HRT, days | 1.0 | 1.1 | 1.1 | 1.1 |
| Sequences/Day | 2 | 3 | 3 | 3 |
| Organic Loading Total COD, g/L/day | 1.45 | 1.49 | 0.99 | 0.51 |
| Suspended Solids Loading | | | | |
| Total, mg/L | 4407 | 4039 | 3203 | 3239 |
| Volatile, mg/L | 3815 | 3016 | 2415 | 2532 |
| % Volatile | 87 | 75 | 75 | 78 |
| F/M (Food to Microbe Ratio) | 0.38 | 0.49 | 0.41 | 0.20 |

Active reactor volume = 13 liters, temperature 35° C., settling time 1.5 hours.

TABLE 2

Performance Data for the ASBR

| Parameter | Organic Loading, g COD/L of Reactor/day | | | |
|---|---|---|---|---|
| | 1.5 | 1.5 | 1.0 | 0.5 |
| Effluent COD | | | | |
| Total, g/L/d | 0.190 | 0.335 | 0.178 | 0.086 |
| Soluble, g/L/d | 0.050 | 0.070 | 0.037 | 0.036 |
| % COD Reductions | | | | |
| Total, % | 86.9 | 77.5 | 82.0 | 83.0 |
| Soluble, % | 96.1 | 94.9 | 96.1 | 92.1 |
| Effluent Suspended Solids | | | | |
| Total, mg/L | 175 | 329 | 177 | 46 |
| Volatile, mg/L | 125 | 222 | 105 | — |
| % Volatile | 71 | 67 | 59 | — |
| Sludge Age, days | 25 | 12 | 18 | 70 |
| pH | 6.8 | 6.9 | 7.0 | 7.4 |
| Alkalinity, mg/l as CaCO₃ | 1760 | 2380 | 2380 | 2240 |
| Volatile Acids, mg/l Acetic | 37 | 47 | 47 | 10 |
| Gas Production (STP), L | 5.6 | 5.6 | 2.9 | 1.3 |
| % Methane | 75.6 | 74.9 | 75 | 75 |

As shown in Table 2, total COD reductions ranged from 77.5 to 86.9% with soluble COD reductions ranging from 92.5 to 96.1%. The effluent total suspended solids ranged from 46 mg/l to 329 mg/l. Another important point from the data is the substrate food to biomass (F/M) ratio. Generally, the lower the F/M ratio the better the performance, in terms of COD reduction and low effluent solids.

Initial research shows excellent performance for low to medium strength liquid by-products. The apparent relationship of F/M ratio to performance suggests higher organic loads can be handled with a higher solids loading. However, higher solids loadings may hamper the settleability of the sludge blanket, similar to maximum solids loading on a clarifier.

This initial example has been on low to medium strength feed substrates using 1 to 1.1 days HRT, and 2 or 3 sequences per day. The ASBR is being applied to high solids by-product streams, as discussed in the next section.

In addition to the fundamental studies reported above, the ASBR has been applied to two by-product wastes having both high organic strengths (COD) and suspended solids (SS). These by-products are from a new industrial plan that specializes in the production of industrial enzymes and other biotechnology products and a manure from a swine confinement feeding facility.

EXAMPLE 2

The by-product material from the industrial enzyme plant that has been used in these studies has the range of characteristics shown in Table 3.

TABLE 3

Characteristics of By-Product Stream from Industrial Plant

| Parameter | Value |
|---|---|
| Total COD (TCOD), g/L | 56.6–67.14 |
| Soluble COD (SCOD), g/L | 20.7–25.1 |
| Total Suspended Solids (TSS), g/L | 27.82 |
| Total Kjeldahl Nitrogen (TKN), g/L | 2.93–3.27 |
| pH | 5.0–6.5 |

The ASBRs are operated using four phases. These phases are: 1) react, 2) settle, 3) decant, and 4) feed. The length of each of these phases can be varied to achieve optimal performance for any given material being treated. The studies on the by-product waste in Table 3 were conducted with a total of three sequences per day (the number of daily sequences can be varied). The time period for each of the four phases and the total cycle time was as follows:

| React | 6 hours |
|---|---|
| Settle | 1.5 hours |
| Decant | 15 minutes |
| Feed | 15 minutes |
| Total cycle time | 8 hours |

The mixing conditions were varied to include continuous mixing during the react and feed cycles (Condition B) and intermittent mixing during the react and feed cycles (Condition A). The mixing time during the intermittent mixing studies was two minutes per hour (2/60). Other operating conditions that were the same for all runs was a hydraulic retention time (HRT) of five days and a temperature of 35° C. The results of the studies on ASBR applications to the industrial by-product stream with the characteristics shown in Table 3 are shown in Table 4.

TABLE 4

Performance of the ASBR under two mixing conditions

| Parameter | Conditions A* | | Condition B** | |
|---|---|---|---|---|
| | Run 1 | Run 2 | Run 1 | Run 2 |
| TCOD Loading, g/L/day | 4.48 | 4.48 | 4.45 | 4.45 |
| Influent TCOD, g/day | 10.07 | 10.07 | 10.0 | 10.0 |
| Effluent TCOD, g/day | 3.24 | 3.56 | 4.53 | 4.88 |
| TCOD Removal, %: | 67.8 | 64.6 | 54.7 | 51.2 |
| Total Biogas Production, L/day | 3.51 | 3.23 | 2.92 | 2.57 |
| Gas Characteristics: | | | | |
| Methane, % | 66.7 | 67.1 | 69.3 | 68.7 |
| Carbon Dioxide, % | 21.3 | 31.8 | 28.9 | 29.2 |
| Nitrogen, % | 2.0 | 1.1 | 1.8 | 2.1 |

TABLE 4-continued
Performance of the ASBR under two mixing conditions

| Parameter | Conditions A* | | Condition B** | |
|---|---|---|---|---|
| | Run 1 | Run 2 | Run 1 | Run 2 |
| CH4,L(STP)/g COD Removed | 0.34 | 0.33 | 0.37 | 0.34 |
| Total Solids Loading, g/L/day | 1.87 | 1.87 | 1.86 | 1.86 |
| Influent Total Solids, g/day | 4.21 | 4.21 | 4.18 | 4.18 |
| Effluent Total Solids, g/day | 1.42 | 1.44 | 1.92 | 2.08 |
| Total Solids Removal, % | 66.3 | 65.8 | 54.1 | 50.2 |
| Solids Retention Time, days | 25.0 | 20.0 | 26.0 | 20.0 |
| $NH_3$—N, mg/l (as N) | 681 | 590 | 564 | 510 |
| Volatile Acids, mg/L as Acetic | 1454 | 1270 | 1842 | 1410 |

*Condition A is intermittent mixing (2 min/hour during react and feed cycles)
**Condition B is continuous mixing during react and feed cycles It is interesting to note form the data in Table 4 that the total COD and total solids destruction were both higher under intermittent mixing conditions than under continuous mixing, even though the solids retention times (SRTs) were nearly identical under the two conditions. This is contrary to what is commonly expected and is a new discovery form this research. It is widely believed that suspended growth anaerobic reactors should be thoroughly mixed on a continuous basis to achieve the highest rates of substrate conversion. This research with the new ASBR system proves that continuous mixing is not needed.

It is also noteworthy that the ASBR performed quite well in the treatment of the very high solids by-product stream (Table 3). Under intermittent mixing conditions, both total solids and COD destruction averaged about 66%.

EXAMPLE 3

Another application of the ASBR that is being investigated is the bioconversion of swine wastes from a confinement feeding facility. These studies have been conducted in plexiglass reactors having a height of 36 inches and a diameter of 5.5 inches. The liquid volume of each reactor is 12 liters. Studies to date have been conducted at both 25° and 35° C. at loadings varying from 1.0 to 5.0 g/L/day. The average characteristics of the raw swine manure are as shown in Table 5.

TABLE 5
Average Characteristics of Raw Swine Manure

| Total Suspended Solids, g/L | 60.7 |
|---|---|
| Volatile Suspended Solids, g/L | 50.4 |
| Total Chemical Oxygen Demand, g/L | 71.5 |
| Total Kjeldahl Nitrogen, TKN, g/L | 4.5 |

Prior to feeding to the reactors, the raw swine manure was diluted by a factor of four to avoid ammonia toxicity in the reactors. Data on performance of the ASBR treating swine wastes were collected at 35° C. and 25° C. The results are shown in Table 6.

TABLE 6
Performance of ASBR Treating Swine Manure at Various Temperatures

| | Temperatures | | | |
|---|---|---|---|---|
| | 35° C. | | 25° C. | |
| | COD Load, g/L/day | | | |
| Parameter | 1 | 3 | 1 | 3 |
| MLSS, g/L | 6.5 | 12.1 | 9.9 | 20.4 |
| MLVSS, g/L | 5.37 | 10.2 | 8.25 | 15.88 |
| Influent TCOD, g/L | 6.0 | 18.1 | 5.82 | 17.5 |
| Influent SCOD, g/L | 2.0 | 6.05 | 1.99 | 5.99 |
| Influent TSS, g/L | 12.25 | 12.75 | 4.58 | 13.79 |
| Influent VSS, g/L | 3.53 | 10.58 | 4.25 | 12.75 |
| Influent pH | 6.2 | 6.2 | 6.2 | 6.2 |
| Effluent TCOD, g/L | 0.813 | 6.913 | 1.475 | 6.210 |
| Effluent SCOD, g/L | 0.407 | 0.407 | 0.343 | 0.965 |
| Effluent TSS, g/L | 0.4 | 4.95 | 0.42 | 5.46 |
| Effluent VSS, g/L | 0.35 | 3.44 | 0.41 | 4.11 |
| Solids Retention Time, days | 110 | 13 | 121 | 21 |
| Effluent pH | 6.7 | 7.0 | 6.9 | 7.0 |
| Gas Production L/d @ STP | 3.98 | 13.5 | 4.94 | 17.16 |
| Gas Composition, % CH4 | 71.6 | 62.7 | 66.4 | 61.3 |
| TCOD Removal, % | 61.8 | 86.4 | 73 | 68 |
| COD conversion to CH4, % | 65.0 | 67.8 | — | — |
| VSS destruction, % | 92.0 | 82.0 | 82.8 | 63.3 |

An important aspect of the swine waste study on the ASBR was the operation of the reactor at two different temperatures, 35° C. and 25° C. Because of the excellent ability of the ASBR to hold biomass within the reactor, it is possible to achieve the same level of methane production over a broad range of temperatures.

The ASBR is capable of significant destruction in volatile solids over a wide range of organic loadings, as measured by chemical oxygen demand (COD), and temperatures. Although volatile solids destruction declines with decreasing temperature, the effect of temperature is not as great at the higher loadings. It is also significant that the undesirable odors commonly associated with swine wastes were virtually eliminated at all COD loadings and temperatures evaluated.

In the ASBR, biological contact and solids separation all occur in the same vessel. No degasification to enhance solids settling is required since the reaction liquid does not leave the reactor during the settling cycle. Thus the partial pressures of the dissolved gases are not reduced, as is the case for an external clarifier, and the tendency for biomass solids to float (due to the release of dissolved gases, primarily carbon dioxide) is greatly reduced.

The basic unique features of the ASBR process is that it makes use of the same tank for both biological reactions and the separation and retention of active biomass with the waste material being converted to methane and carbon dioxide. The internal biomass separation (as opposed to external degasification and solids separation in a clarifier) is the fundamental unique feature of the ASBR.

An important observation from the above Examples is that the process does no require continuous mixing and that performance is actually enhanced by intermittent mixing. In experiments comparing two ASBRs, one continuously mixed and the other mixed only two (2) minutes out of each 60 minutes, the intermittently-mixed ASBR achieved a higher degree of waste conversion to biogas than did the continuously mixed reactor. Thus, the ASBR reaction liquid need not be mixed on a continuous basis. This, of course, is an energy saving feature and also leads to improved performance of the system.

The rate of internal biomass separation during the settling cycle can be enhanced by drawing a partial vacuum on the gas over the reaction liquid in the reactor for a short period of time just prior to the settling cycle. The ASBR that makes use of the vacuum enhancement is referred to as the "vacuum enhanced anaerobic sequencing batch reactor".

Gas bubbles which form on the surface of the microorganisms in the flocculent or granular biomass exert a lifting effect on the suspended solids, thus inhibiting the rate of settling. Although the biomass solids settle well without the vacuum, the partial vacuum will increase the rate of biomass settling in the reactor and therefore shorten the settling cycle. Also, vacuum enhancement leads to a higher concentration of biomass in the reactor and higher rates of waste conversion to biogas.

The method of mixing the ASBR reactor contents is not critical. The reaction liquid may be mixed by gas recirculation, mechanical turbines, or by liquid recycle. However, when the "vacuum enhanced" option is used, it would not be practical to mix by gas recirculation. In that case, the mechanical or hydraulic mixing option should be used. It is also significant that mixing of the ASBR contents should not be too violent. Violent mixing tends to sheer the flocculent and granular biomass solids, resulting in poor settling.

The ASBR is capable of achieving high levels of conversion of organic wastes to biogas over a wide range of temperatures. Common temperatures of operation are in the mesophilic (30°-40° C.) and the thermophilic (50°-60° C.) range of temperatures. However, in experiments on swine wastes, methane production rates achieved at 25° C. were equal to those achieved at 35° C. The ASBR is capable of compensating for reduced temperatures (and the resulting reduced metabolic rates of the microorganisms) by increasing the population of microorganisms in the reactor. This is possible as a result of the reduced rates of microbial decay (endogenous respiration) that occur at lower temperatures as compared with higher temperatures. In essence, the ASBR is capable of operation over a range of temperatures from a low of about 10° C. to a high of about 65° C. The only limiting factor is the ability to hold solids in the reactor through internal settling in order to achieve the longer solids retention times required at the lower temperatures.

While only certain preferred embodiments of this invention have been shown and described by way of illustration, many modifications will occur to those skilled in the art and it is, therefore, desired that it be understood that it is intended herein to cover all such modifications that fall within the true spirit and scope of this invention.

I claim:

1. A method of producing biogas from waste containing organic biomass, comprising the steps of:
   feeding the waste into a vessel until a predetermined full liquid level is reached;
   maintaining anaerobic reaction conditions of the waste including mixing in the vessel to produce biogas;
   discontinuing the mixing to allow the biomass to settle in the vessel resulting in the formation of a low suspended solid supernatant;
   decanting the supernatant from the vessel until a predetermined lower liquid level is reached; and
   repeating in sequence the feeding step, reacting step, settling step, and decanting step.

2. The method of claim 1 wherein mixing during the reacting step is intermittent.

3. The method of claim 1 wherein mixing during the reacting step is continuous.

4. The method of claim 1 wherein mixing is accomplished by recycling fluid in the vessel 5. The method of claim 4 wherein the recycling fluid is the biogas.

6. The method of claim 4 wherein the recycling fluid is the waste.

7. The method of claim 1 further including mixing of the waste during the feeding step.

8. The method of claim 7 wherein mixing during the feeding step is intermittent.

9. The method of claim 7 wherein mixing during the feeding step is continuous.

10. The method of claim 7 wherein mixing is accomplished by recycling fluid in the vessel.

11. The method of claim 10 wherein the recycling fluid is the biogas.

12. The method of claim 10 wherein the recycling fluid is the waste.

13. The method of claim 1 further including the step of applying a partial vacuum to a head space of the vessel immediately prior to the settling step.

14. The method of claim 13 wherein mixing during the reacting step is accomplished by recycling waste.

15. The method of claim 1 further including the step of wasting excess biomass from a bottom section of the reactor on a periodic basis immediately prior to the feeding step.

16. The method of claim 1 wherein the anaerobic reaction conditions include operating temperatures in the vessel in the range of about 10° C. to about 65° C.

17. The method of claim 1 wherein the anaerobic reaction conditions include the presence of a mixed consortium of anaerobic microorganisms.

18. The method of claim 17 wherein the microorganisms are selected from a group consisting of hydrolytic, acetogenic and methanogenic bacteria.

* * * * *

UNITED STATES PATENT AND TRADEMARK OFFICE
CERTIFICATE OF CORRECTION

PATENT NO. : 5,185,079
DATED : February 9, 1993
INVENTOR(S) : Richard R. Dague

It is certified that error appears in the above-indentified patent and that said Letters Patent is hereby corrected as shown below:

At column 1, between the Title and Background Art, insert the following:

--Government Support

This invention was made with government support under Grant No. 89-34188-43 awarded by the United States Department of Agriculture. The U.S. Government has certain rights in the invention.

Technical Field

This invention relates to methods of anaerobic bioconversions of organic wastes, and more particularly an anaerobic sequence batch process carried out in a single vessel.--

At column 3, line 7, delete "form" and substitute --from--.

At column 3, line 8, delete "nomical" and substitute --nominal--.

UNITED STATES PATENT AND TRADEMARK OFFICE
CERTIFICATE OF CORRECTION

PATENT NO. : 5,185,079
DATED : February 9, 1993
INVENTOR(S) : Richard R. Dague

It is certified that error appears in the above-indentified patent and that said Letters Patent is hereby corrected as shown below:

At column 5, line 31, delete "form" and substitute --from--.

Signed and Sealed this

Eleventh Day of April, 1995

Attest:

BRUCE LEHMAN

Attesting Officer        Commissioner of Patents and Trademarks